（12） United States Patent
Muzslay

(10) Patent No.: US 8,292,951 B2
(45) Date of Patent: Oct. 23, 2012

(54) TETHERED POP UP BRANCH STRUCTURE STENT GRAFT AND METHOD

(75) Inventor: Heath Muzslay, Petaluma, CA (US)

(73) Assignee: Medtronic Vascular, Inc., Santa Rosa, CA (US)

(*) Notice: Subject to any disclaimer, the term of this patent is extended or adjusted under 35 U.S.C. 154(b) by 238 days.

(21) Appl. No.: 12/770,556

(22) Filed: Apr. 29, 2010

(65) Prior Publication Data

US 2011/0270385 A1    Nov. 3, 2011

(51) Int. Cl.
*A61F 2/06*    (2006.01)
(52) U.S. Cl. ............... 623/1.35; 623/1.13; 623/1.15
(58) Field of Classification Search ............... 623/1.13, 623/1.35, 1.15; *A61F 2/06*
See application file for complete search history.

(56) References Cited

U.S. PATENT DOCUMENTS

| | | |
|---|---|---|
| 3,692,618 A | 9/1972 | Dorschner et al. |
| 3,802,817 A | 4/1974 | Matsuki et al. |
| 4,340,563 A | 7/1982 | Appel et al. |
| 5,387,235 A | 2/1995 | Chuter |
| 5,456,713 A | 10/1995 | Chuter |
| 5,693,084 A | 12/1997 | Chuter |
| 5,709,713 A | 1/1998 | Evans et al. |
| 5,720,776 A | 2/1998 | Chuter et al. |
| 5,755,772 A | 5/1998 | Evans et al. |
| 5,800,514 A | 9/1998 | Nunez et al. |
| 6,248,097 B1 | 6/2001 | Beitz et al. |
| 6,465,073 B1 | 10/2002 | Morman et al. |
| 6,565,597 B1 | 5/2003 | Fearnot et al. |
| 6,994,724 B2 | 2/2006 | Schmitt |
| 7,189,257 B2 | 3/2007 | Schmitt et al. |
| 7,264,632 B2 | 9/2007 | Wright et al. |
| 2003/0199967 A1 | 10/2003 | Hartley |
| 2005/0143806 A1 | 6/2005 | Phillips |
| 2006/0229561 A1 | 10/2006 | Huszar |

(Continued)

FOREIGN PATENT DOCUMENTS

EP    0556749    2/1993

(Continued)

OTHER PUBLICATIONS

U.S. Appl. No. 12/425,616, filed Apr. 2009, Bruszewski et al.
U.S. Appl. No. 12/425,628, filed Apr. 2009, Bruszewksi et al.

*Primary Examiner* — Christopher D Koharski
*Assistant Examiner* — Jason-Dennis Stewart

(57) ABSTRACT

A method includes tethering a first pop up branch structure of a tethered pop up branch structure stent graft to a second pop up branch structure of the tethered pop up branch structure stent graft with a tether. The tethered pop up branch structure stent graft is deployed into a main vessel such that the first pop up branch structure is near a first branch vessel emanating from the main vessel and the second pop up branch structure is near a second branch vessel emanating from the main vessel. A first guide is passed through a first collateral opening in the first pop up branch structure and into the first branch vessel. A second guide is passed through a second collateral opening in the second pop up branch structure and into the second branch vessel. The tether is then removed such that the first pop up branch structure slides outwards on the first guide and into a first ostium of the first branch vessel and the second pop up branch structure slides outwards on the second guide into a second ostium of the second branch vessel.

7 Claims, 5 Drawing Sheets

U.S. PATENT DOCUMENTS

| | | |
|---|---|---|
| 2006/0276883 A1 | 12/2006 | Greenberg et al. |
| 2007/0135904 A1 | 6/2007 | Eidenschink |
| 2007/0244542 A1 | 10/2007 | Greenan |
| 2008/0114442 A1 | 5/2008 | Mitchel et al. |
| 2008/0262590 A1 | 10/2008 | Murray |
| 2009/0264991 A1 * | 10/2009 | Paul et al. .................... 623/1.35 |
| 2009/0276027 A1 | 11/2009 | Glynn |

FOREIGN PATENT DOCUMENTS

| | | |
|---|---|---|
| EP | 1201212 | 5/2002 |
| WO | WO93/16669 | 9/1993 |
| WO | WO 2005/034809 | 4/2005 |
| WO | WO2005/037160 | 4/2005 |
| WO | WO 2006/113501 | 10/2006 |

* cited by examiner

TETHERED POP UP BRANCH STRUCTURE STENT GRAFT AND METHOD

BACKGROUND OF THE INVENTION

1. Field of the Invention

The present invention relates to an intra-vascular device and method. More particularly, the present invention relates to a device for treatment of intra-vascular diseases.

2. Description of Related Art

A conventional main (vessel) stent graft typically includes a radially expandable reinforcement structure, formed from a plurality of annular stent rings, and a cylindrically shaped layer of graft material, sometimes called graft cloth, defining a lumen to which the stent rings are coupled. Main stent grafts are well known for use in tubular shaped human vessels.

To illustrate, endovascular aneurysmal exclusion is a method of using a main stent graft to exclude pressurized fluid flow from the interior of an aneurysm, thereby reducing the risk of rupture of the aneurysm and the associated invasive surgical intervention.

Main stent grafts with custom side openings are sometimes fabricated to accommodate the particular vessel structure of each individual patient. Specifically, as the location of branch vessels emanating from a main vessel, e.g., having the aneurysm, varies from patient to patient, main stent grafts are fabricated with side openings customized to match the position of the branch vessels of the particular patient. However, custom fabrication of main stent grafts is relatively expensive and time consuming.

SUMMARY OF THE INVENTION

A method includes tethering a first pop up branch structure of a tethered pop up branch structure stent graft to a second pop up branch structure of the tethered pop up branch structure stent graft with a tether. The tethered pop up branch structure stent graft is deployed into a main vessel such that the first pop up branch structure is near a first branch vessel emanating from the main vessel and the second pop up branch structure is near a second branch vessel emanating from the main vessel.

A first guide is passed through a first collateral opening in the first pop up branch structure and into the first branch vessel. A second guide is passed through a second collateral opening in the second pop up branch structure and into the second branch vessel. The tether is then removed such that the first pop up branch structure slides outwards on the first guide and into a first ostium of the first branch vessel and the second pop up branch structure slides outwards on the second guide into a second ostium of the second branch vessel.

Thus, even when the particular vessel structure of the patient results in an initial predeployment misalignment between the first and second pop up branch structures and the first and second ostia, by tethering the first and second pop up branch structures together, inserting guides into the first and second collateral openings, and then releasing the first and second pop up branch structures as described above, the first and second collateral openings are accurately placed within the first and second ostia.

Accordingly, use of the tether allows the design of the tethered pop up branch structure stent graft to be used with a wide range of vessel structures found in different patients thus avoiding formation of custom stent grafts with custom side openings for each patient. In this manner, the cost and time of the procedure is minimized.

Embodiments are best understood by reference to the following detailed description when read in conjunction with the accompanying drawings.

BRIEF DESCRIPTION OF THE DRAWINGS

Common reference numerals are used throughout the drawings and detailed description to indicate like elements.

DETAILED DESCRIPTION

Figure 1:
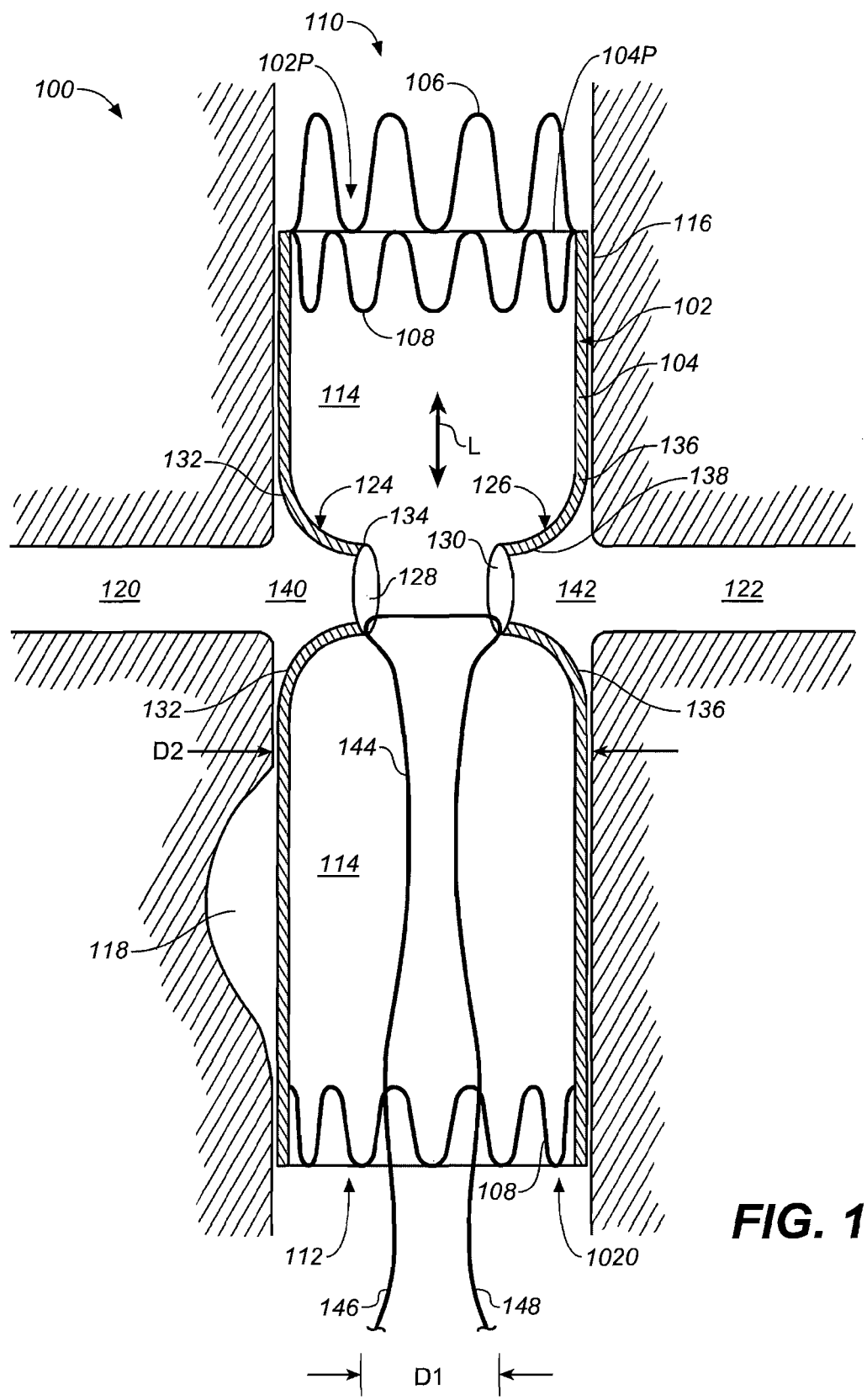
FIG. 1 is a cross-sectional view of a vessel assembly including a tethered pop up branch structure stent graft in accordance with one example.

As an overview and in accordance with one example, referring to FIG. 1, a method includes tethering a first pop up branch structure 124 of a tethered pop up branch structure stent graft 102 to a second pop up branch structure 126 of tethered pop up branch structure stent graft 102 with a tether 144. Tethered pop up branch structure stent graft 102 is deployed into a main vessel 116 such that first pop up branch structure 124 is near a first branch vessel 120 emanating from main vessel 116 and second pop up branch structure 126 is near a second branch vessel 122 emanating from main vessel 116.

Figure 2:
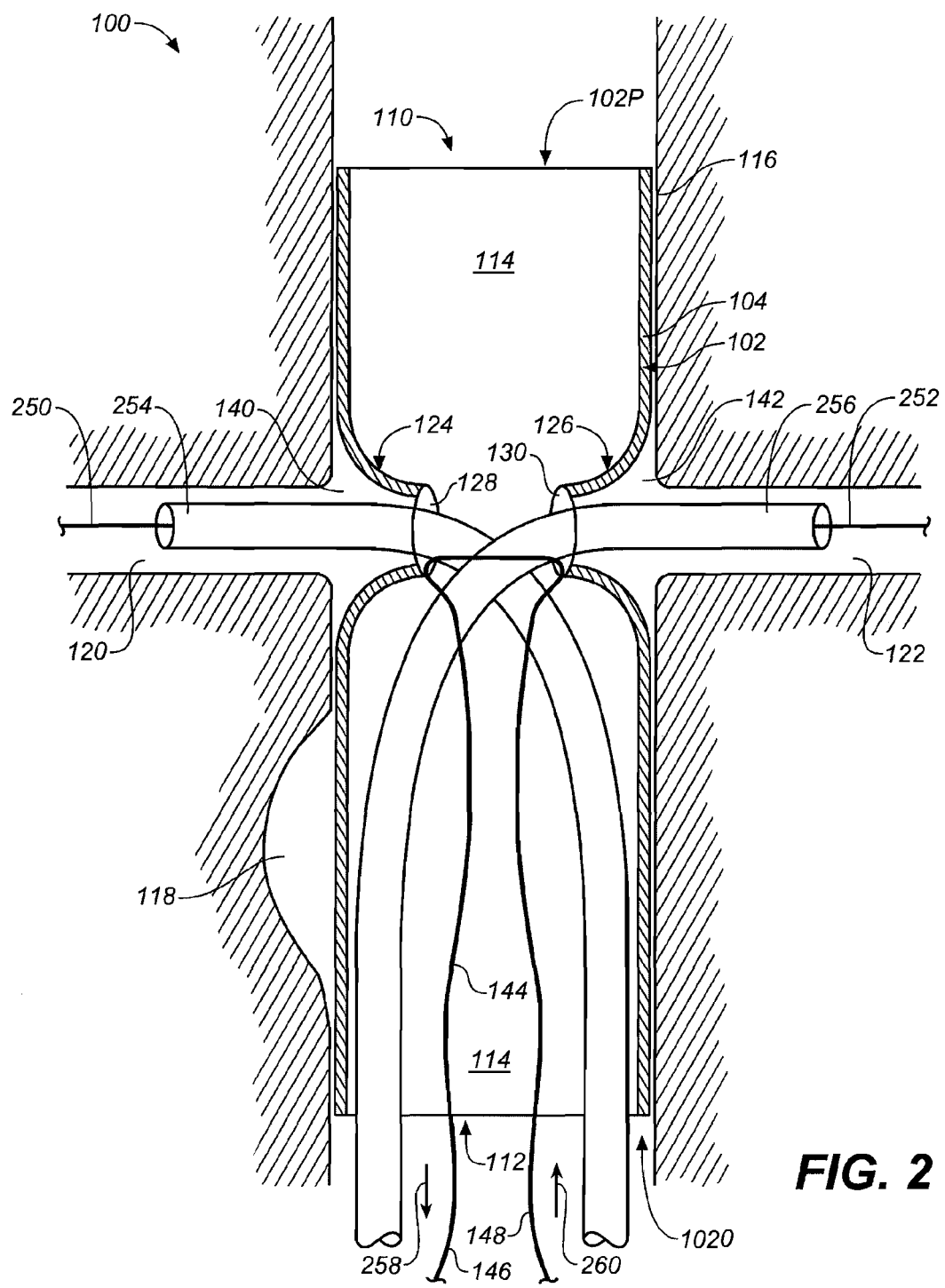
FIGS. 2, 3, 4 are cross-sectional views of the vessel assembly of FIG. 1 at later stages during deployment of the tethered pop up branch structure stent graft in accordance with various examples.

Referring now to FIG. 2, a first guide 254 is passed through a first collateral opening 128 in first pop up branch structure 124 and into first branch vessel 120. A second guide catheter 256 is passed through a second collateral opening 130 in second pop up branch structure 126 and into second branch vessel 122. In alternate delivery systems, such guide tubes may be small and be prepositioned to have their distal ends each extend into the first and the second collateral openings 124, 126. They may be compressed within the delivery system, so that upon deployment of the main body, the prepositioned guide tubes can be used to avoid the need to cannulate the branch openings 124, 126 during the delivery procedure. Guide tubes so situated will act as a guide for subsequently inserted guide wires and/or larger guide catheters which can be used to deliver and deploy side branch prostheses with a minimum of difficulty associated with guiding catheters and wires into the side branches. See the description of such small tubes as described in Patent Application of Bruszewski et al., U.S. patent application Ser. No. 12/770,566, filed on Apr. 29 2010, entitled "MOBILE EXTERNAL COUPLING FOR BRANCH VESSEL CONNECTION", which is herein incorporated by reference in its entirety.

Figure 3:
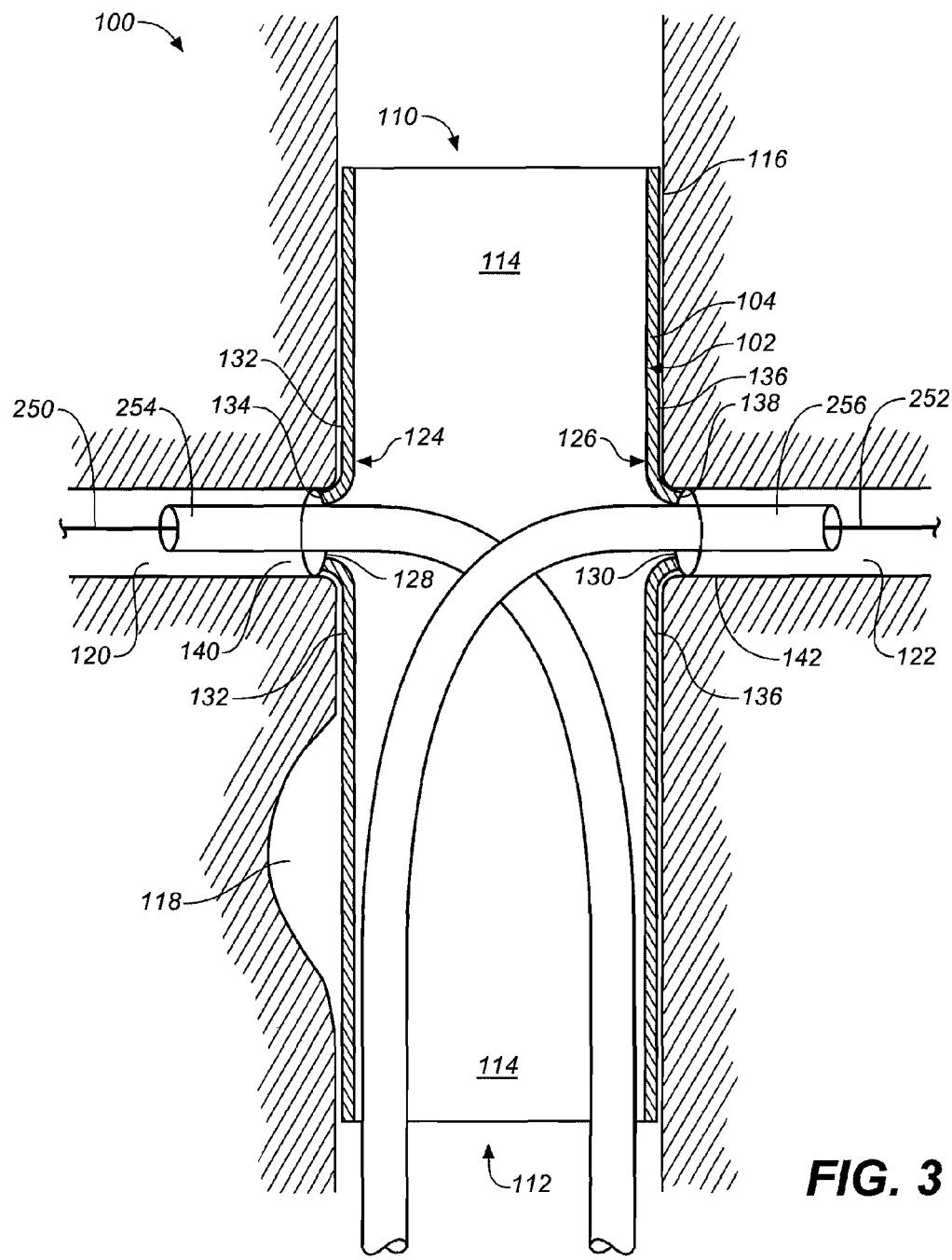

Referring now to FIGS. 2 and 3 together, tether 144 is then removed such that first pop up branch structure 124 slides outwards on first guide 254 and into a first ostium 140 of first branch vessel 120 and second pop up branch structure 126 slides outwards on second guide 256 into a second ostium 142 of second branch vessel 122 as illustrated in FIG. 3.

Thus, even when the particular vessel structure of the patient results in an initial predeployment misalignment between pop up branch structures 124, 126 and ostia 140, 142, by tethering pop up branch structures 124, 126, inserting guides 254, 256 into collateral openings 128, 130, and then releasing pop up branch structures 124, 126, collateral openings 128, 130 are accurately placed within ostia 140, 142, respectively.

Accordingly, use of tether 144 allows the design of tethered pop up branch structure stent graft 102 to be used with a wide range of vessel structures found in different patients thus avoiding formation of custom stent grafts with custom side openings for each patient. In this manner, the cost and time of the procedure is minimized.

Now in more detail, FIG. 1 is a cross-sectional view of a vessel assembly 100 including a tethered pop up branch structure stent graft 102 in accordance with one example. Referring now to FIG. 1, tethered pop up branch structure stent graft 102 includes a graft material 104, e.g., formed of ePTFE, polyester or Dacron material, and a plurality of resilient self-expanding support structures, e.g., formed of super elastic self-expanding memory material such as nitinol. Graft material 104 includes a proximal end 104P.

The support structures include a proximal anchor stent ring 106 at a proximal end 102P of tethered pop up branch structure stent graft 102 and one or more stent rings 108 distal to proximal anchor stent ring 106. Proximal anchor stent ring 106 is attached to proximal end 104P of graft material 104. Proximal anchor stent ring 106 and stent rings 108 are attached to graft material 104, e.g., by sutures, adhesive, or other means.

Tethered pop up branch structure stent graft 102 includes a proximal main opening 110 at proximal end 102P of tethered pop up branch structure stent graft 102 and a distal main opening 112 at a distal end 102D of tethered pop up branch structure stent graft 102. Further, tethered pop up branch structure stent graft 102 includes a longitudinal axis L. A main lumen 114 is defined by tethered pop up branch structure stent graft 102 and extends generally parallel to longitudinal axis L and between proximal main opening 110 and distal main opening 112 of tethered pop up branch structure stent graft 102.

As used herein, the proximal end of a prosthesis such as a stent graft is the end closest to the heart via the path of blood flow whereas the distal end is the end furthest away from the heart during deployment. In contrast and of note, the distal end of the catheter is usually identified to the end that is farthest from the operator (handle) while the proximal end of the catheter is the end nearest the operator (handle).

For purposes of clarity of discussion, as used herein, the distal end of the catheter is the end that is farthest from the operator (the end furthest from the handle) while the distal end of the prosthesis is the end nearest the operator (the end nearest the handle), i.e., the distal end of the catheter and the proximal end of the stent graft are the ends furthest from the handle while the proximal end of the catheter and the distal end of the stent graft are the ends nearest the handle. However, those of skill in the art will understand that depending upon the access location, the stent graft and delivery system description may be consistent or opposite in actual usage.

Tethered pop up branch structure stent graft 102 is deployed into a main vessel 116. Main vessel 116, e.g., the aorta, includes an aneurysm 118. Tethered pop up branch structure stent graft 102, sometimes called a prosthesis, is deployed into main vessel 116 to exclude aneurysm 118 using any one of a number of techniques well known to those of skill in the art.

Emanating from main vessel 116 is a first branch vessel 120 and a second branch vessel 122, sometimes called visceral branches of the abdominal aorta. The location of branch vessels 120, 122 vary from patient to patient. Examples of branch vessels include the renal arteries (RA) and the superior mesenteric artery (SMA).

Proximal anchor stent ring 106 and stent rings 108 are self-expanding facilitating expansion, fixation, and sealing of tethered pop up branch structure stent graft 102 into main vessel 116. In another example, a tethered pop up branch structure stent graft similar to tethered pop up branch structure stent graft 102 is formed with stent rings that are balloon expanded facilitating fixation and sealing of the tethered pop up branch structure stent graft into main vessel 116.

Although three stent rings 106, 108 are illustrated, in other examples, a tethered pop up branch structure stent graft similar to tethered pop up branch structure stent graft 102 is formed with more or less than three stent rings or other self-expanding members. Stent rings 106, 108 are not illustrated in the remaining figures for clarity of presentation.

Tethered pop up branch structure stent graft 102 further includes a first pop up branch structure 124 and a second pop up branch structure 126, sometimes called "volcanoes" or mobile external couplings. First pop up branch structure 124 and second pop up branch structure 126 include a first collateral opening 128 and a second collateral opening 130, respectively. Collateral openings 128, 130, sometimes called side openings, are openings within graft material 104.

In one example, pop up branch structures 124, 126 are disposed on an outside surface of tethered pop branch structure stent graft 102 at collateral openings 128, 130 in graft material 104. Pop up branch structures 124, 126 are generally frustoconically shaped. Pop up branch structures 124, 126 can include graft material coupled to helical stents. The graft material is preferably the same type as graft material 104 and is preferably a continuation of graft material 104, although the graft material can be a separate piece of graft material attached to graft material 104.

Pop up branch structure 124 includes a base 132 and a top 134, sometimes called a first base and a first top. Similarly, pop up branch structure 126 includes a base 136 and a top 138, sometimes called a second base and a second top. Although pop up branch structures 124, 126 are described as generally frustoconical in shape, bases 132, 136 are suitably generally elliptical rather than circular. Bases 132 generally lie upon the imaginary cylindrical surface defined by graft material 104. Tops 134, 138 define collateral openings 128, 130, respectively, which are suitably circular.

Structures similar to pop up branch structures 124, 126 are described in (1) Bruszewski et al., U.S. patent application Ser. No. 12/425,628, filed on 17 Apr. 2009, entitled "MOBILE EXTERNAL COUPLING FOR BRANCH VESSEL CONNECTION"; (2) Bruszewski et al., U.S. patent application Ser. No. 12/425,616, filed on 17 Apr. 2009, entitled "MOBILE EXTERNAL COUPLING FOR BRANCH VESSEL CONNECTION"; and Bruszewski et al., U.S. patent application Ser. No. 12/770,566, filed on Apr. 29, 2010, entitled "MOBILE EXTERNAL COUPLING FOR BRANCH VESSEL CONNECTION", which are all herein incorporated by reference in their entireties.

Tethered pop up branch structure stent graft 102 is deployed such that pop up branch structures 124, 126 and more particularly collateral openings 128, 130 are generally aligned with branch vessels 120, 122, respectively. Stated another way, tethered pop up branch structure stent graft 102 is deployed such that pop up branch structures 124, 126 and more particularly collateral openings 128, 130 are adjacent or near ostia (plural of ostium) 140, 142 of branch vessels 120, 122, respectively. Suitably, pop up branch structures 124, 126 and, more particularly, collateral openings 128, 130 are slightly distal of ostia 140, 142 thus facilitating insertion of catheters through collateral openings 128, 130, ostia 140, 142 and into branch vessels 120, 122, respectively, as discussed further below.

Once anchored within main vessel 116, blood flows through main lumen 114 and more generally through tethered pop up branch structure stent graft 102 thus excluding aneurysm 118. Further, pop up branch structures 124, 126 allows branch vessels 120, 122 to be perfused through collateral openings 128, 130, respectively. More particularly, the pressure inside of tethered pop up branch structure stent graft 102 is greater than the pressure within branch vessels 120, 122. Due to this pressure differential, blood flows through collateral openings 128, 130 and into branch vessels 120, 122, respectively.

To prevent pop up branch structures 124, 126 from being forced outward due to the blood pressure differential, pop up branch structures 124, 126 are tethered with a tether 144. More particularly, tether 144 is a structure that anchors pop up branch structures 124, 126 together.

By tethering pop up branch structures 124, 126 together, pop up branch structures are prevented from being deployed in the wrong positions, i.e., at positions not corresponding to ostia 140, 142 of branch vessels 120, 122, respectively. Specifically, as the location of branch vessels 120, 122 varies from patient to patient, there will typically be some degree of misalignment between pop up branch structures 124, 126 including collateral openings 128, 130 and ostia 140, 142 of branch vessels 120, 122, respectively. If pop up branch structures 124, 126 were not tethered by tether 144, there is a risk that pop up branch structures 124, 126 would be force outward and into the wall of main vessel 116 instead of into branch vessels 120, 122. This would cause collateral openings 128, 130 to be covered by the wall of main vessel 116 thus occluding collateral openings 128, 130. In other words, if pop up branch structures 124, 126 were not tethered by tether 144, pop up branch structures 124, 126 would be deployed somewhat uncontrollably and thus unpredictably.

In one example, tether 144 is a single continuous suture that sutures (attaches) pop up branch structures 124, 126, e.g., tops 134, 138 thereof, to one another. Tether 144 extends through the graft material of pop up branch structures 124, 126, i.e., is stitched to pop up branch structures 124, 126, e.g., at tops 134, 138. In one example, tether 144 is a single stitch between pop up branch structures 124, 126 facilitating easy removal of tether 144.

As tether 144 is a single continuous suture in one example, tether 144 has two ends 146, 148. Tether 144 extends proximally (towards the handle) from pop up branch structures 124, 126 though main lumen 114, through the lumen of the graft cover (not shown) and exits the patient, e.g., through a luer fitting. More particularly, at least one of ends 146, 148 exits the patient.

In other examples, tether 144 is a wire, chord, or other structure that holds pop up branch structures 124, 126 together. Further, tether 144 can include knots, loops, clasps or other structures that release pop up branch structures 124, 126 when pulled.

Tether 144 anchors tops 134, 138 of pop up branch structures 124, 126 inwards of graft material 104. More particularly, a distance Dl between tops 134, 138 of pop up branch structures 124, 126 is less than the diameter D2 of graft material 104 (and the distance between bases 132, 136) when deployed. Accordingly, tops 134, 138 of pop up branch structures 124, 126 are spaced inwards of the wall of main vessel 116 thus preventing occlusion of collateral openings 128, 130. Further, collateral openings 128, 130 are spaced apart from ostia 140, 142 facilitating insertion of catheters therein as discussed in reference to FIG. 2.

FIG. 2 is a cross-sectional view of vessel assembly 100 of FIG. 1 at a later stage during deployment of tethered pop up branch structure stent graft 102 in accordance with one example. Referring now to FIG. 2, guide wires 250, 252 extend from inside main lumen 114 of tethered pop up branch structure stent graft 102, though collateral openings 128, 130 of pop up branch structures 124, 126 and into branch vessels 120, 122, respectively.

Catheters 254, 256, e.g., including hollow tubes, are advanced over guide wires 250, 252 to extend from inside main lumen 114 of tethered pop up branch structure stent graft 102, though collateral openings 128, 130 of pop up branch structures 124, 126 and into branch vessels 120, 122, respectively. Use and deployment of guide wires and catheters similar to guide wires 250, 252 and catheters 254, 256 are well known to those of skill in the art and the particular technique used is not essential. In one example, introducers are used to facilitate placement of guide wires 250, 252 and/or catheters 254, 256.

In another example, only guide wires 250, 252 are used as described and catheters 254, 256 are not used in accordance with this example. Although deployment of pop up branch structures 124, 126 using catheters 254, 256 is illustrated and discussed below, in light of this disclosure, those of skill in the art will understand that the discussion is equally applicable to the deployment of pop up branch structures 124, 126 using guide wires 250, 252 or other guide structures in the case when catheters 254, 256 are not used.

As further illustrated in FIG. 2, guide wires 250, 252 and catheters 254, 256 are deployed through collateral openings 128, 130 while pop up branch structures 124, 126 remain tethered with tether 144 as discussed above.

Once guide wires 250, 252 and catheters 254, 256 are deployed through collateral openings 128, 130 as illustrated in FIG. 2, pop up branch structures 124, 126 can be released from tether 144 without risk of misalignment between pop up branch structures 124, 126 including collateral openings 128, 130 and ostia 140, 142 of branch vessels 120, 122 as discussed below.

FIG. 3 is a cross-sectional view of vessel assembly 100 of FIG. 2 at a later stage during deployment of tethered pop up branch structure stent graft 102 in accordance with one example. Referring now to FIGS. 2 and 3 together, tether 144 is removed to release, sometimes called untether, pop up branch structures 124, 126. In one example, to remove tether 144, end 146 (or end 148) is pulled proximally as indicated by arrow 258 causing end 148 (or end 146) to move distally as indicated by arrow 260. End 148 (or end 146) thus slips out of pop up branch structures 124, 126 releasing pop up branch structures 124, 126 from each other. Tether 144 is pulled until end 148 (or end 146) is removed from the patient thus completely removing tether 144.

In light of this disclosure, those of skill in the art will understand that any one of a number of delivery catheters can be designed to facilitate removal of tether 144 and the particular catheter used is not essential.

Upon removal of tether 144, pop up branch structures 124, 126 slide outwards along catheters 254, 256 (or guide wires 250, 252 in the event catheters 254, 256 are not used). More particularly, blood pressure forces pop up branch structures 124, 126 outwards and into ostia 140, 142. Catheters 254, 256 are guides insuring that collateral openings 128, 130 are located within ostia 140, 142, respectively.

Further, even when the particular vessel structure of the patient results in an initial predeployment misalignment between pop up branch structures 124, 126 and ostia 140, 142, by tethering pop up branch structures 124, 126, inserting guides (e.g., catheters 254, 256) into collateral openings 128, 130, and then releasing pop up branch structures 124, 126, collateral openings 128, 130 are accurately placed within ostia 140, 142, respectively. Accordingly, use of tether 144 allows the design of tethered pop up branch structure stent graft 102 to be used with a wide range of vessel structures found in different patients thus avoiding formation of custom stent grafts with custom side openings for each patient. In this manner, the cost and time of the procedure is minimized.

Figure 4:
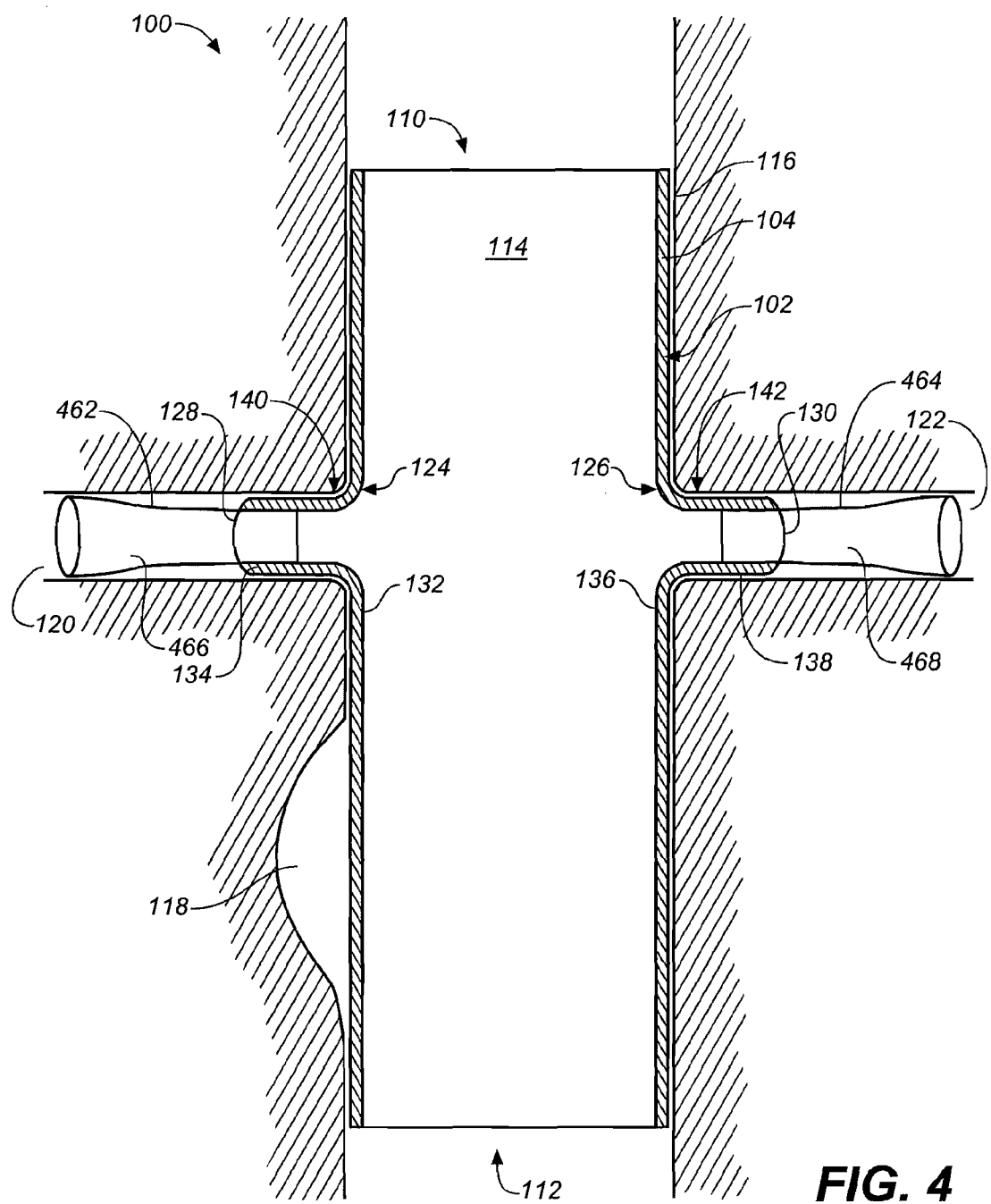

FIG. 4 is a cross-sectional view of vessel assembly 100 of FIG. 3 at a later stage during deployment of tethered pop up branch structure stent graft 102 in accordance with one example. Referring now to FIGS. 3 and 4 together, branch prostheses (plural of prosthesis) 462, 464, e.g., stents, are deployed into branch vessels 120, 122 using any one of a number of techniques well known to those of skill in the art. Illustratively, branch prostheses 462, 464 are advanced through catheters 254, 256 and over guide wires 250, 252 and deployed. Catheters 254, 256 and guide wires 250, 252 are then removed.

Branch prostheses 462, 464 are located with collateral openings 128, 130 and engage tethered pop up branch structure stent graft 102. More particularly, branch prostheses 462, 464 are engaged with pop up branch structures 124, 126 and branch vessels 120, 122 thus fixing pop up branch structures 124, 126 in place within branch vessels 120, 122, respectively.

Branch prostheses 462, 464 define branch lumens 466, 468 therein. Blood flow flows through branch lumens 466, 468 thus perfusing branch vessels 120, 122.

Figure 5:
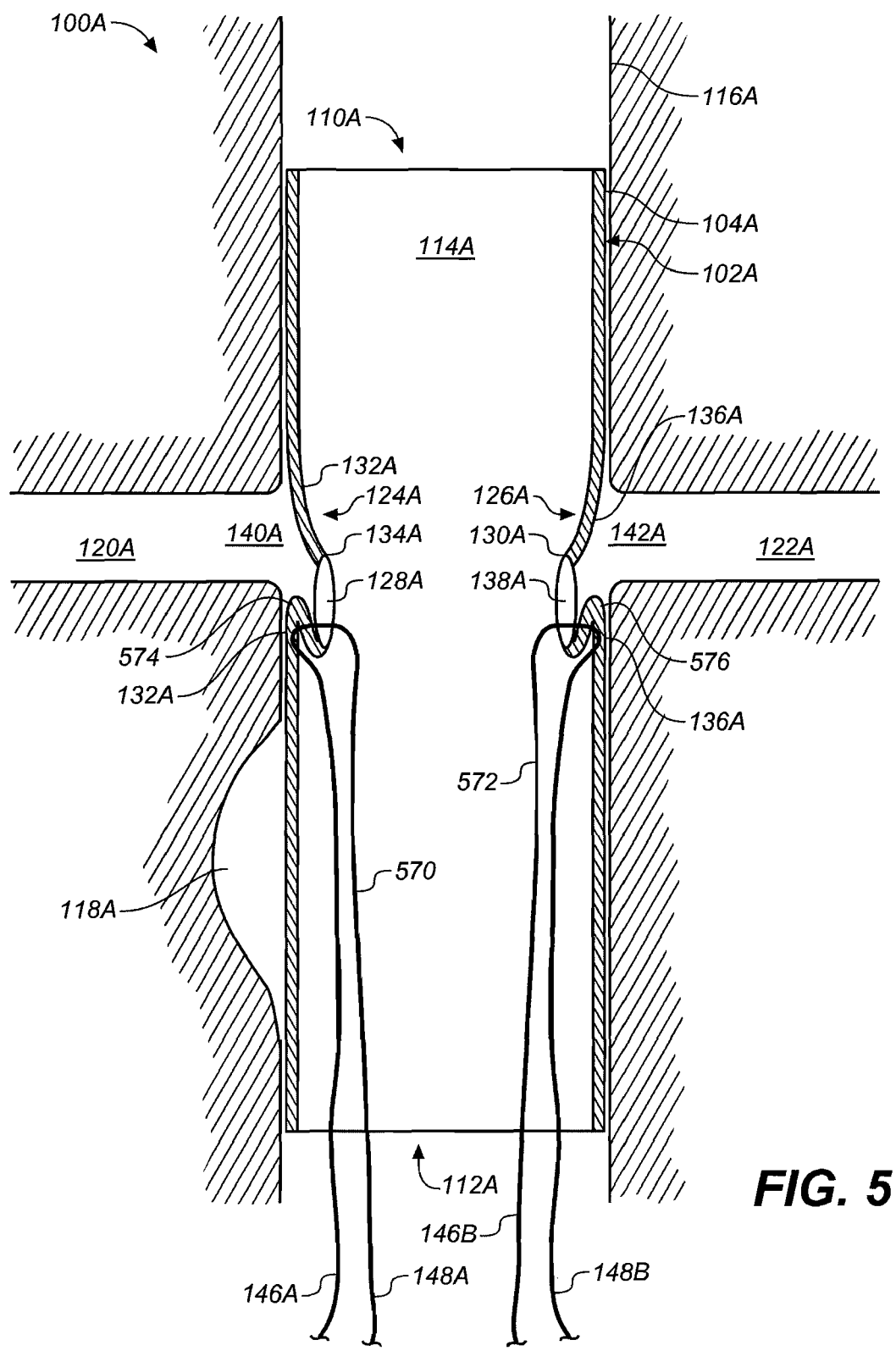
FIG. 5 is a cross-sectional view of a vessel assembly including a tethered pop up branch structure stent graft in accordance with another example.

FIG. 5 is a cross-sectional view of a vessel assembly 100A including a tethered pop up branch structure stent graft 102A in accordance with another example. Vessel assembly 100A of FIG. 5 includes branch structure stent graft 102A, a graft material 104A, a proximal main opening 110A, a distal main opening 112A, a main lumen 114A, a main vessel 116A, an aneurysm 118A, branch vessels 120A, 122A, pop up branch structures 124A, 126A, collateral openings 128A, 130A, bases 132A, 136A, tops 134A, 138A, and ostia 140A, 142A similar or identical to branch structure stent graft 102, graft material 104, proximal main opening 110, distal main opening 112, main lumen 114, main vessel 116, aneurysm 118, branch vessels 120, 122, pop up branch structures 124, 126, collateral openings 128, 130, bases 132, 136, tops 134, 138, and ostia 140, 142 of vessel assembly 100 of FIG. 1. Only the significant differences between vessel assembly 100A and vessel assembly 100 are discussed below.

Referring now to FIG. 5, pop up branch structures 124A, 126B are tethered with tethers 570, 572, respectively. More particularly, tethers 570, 572, sometimes called first and second tethers, are structures that anchor pop up branch structures 124A, 126A to graft material 104A of tethered pop up branch structure stent graft 102A.

By tethering pop up branch structures 124A, 126A to graft material 104A, pop up branch structures 124A, 126A are prevented from being deployed in the wrong positions, i.e., at positions not corresponding to ostia 140A, 142A of branch vessels 120A, 122A.

In one example, tethers 570, 572 are single continuous sutures that suture (attach) pop up branch structures 124A, 126A, e.g., tops 134A, 138A thereof, to the inside of graft material 104A. As tethers 570, 572 are single continuous sutures in one example, tethers 570, 572 each have a first end 146A, 146B and a second end 148A, 148B, respectively. tethers 570, 572 extend proximally (towards the handle) from pop up branch structures 124A, 126A though main lumen 114A, through the lumen of the graft cover (not shown) and exits the patient, e.g., through a luer fitting. More particularly, at least one of ends 146A, 148A and ends 146B, 148B exits the patient.

To further illustrate, tether 570 extends through the graft material of pop up branch structure 124A, i.e., is stitched to pop up branch structure 124A, e.g., at top 134A, and is also stitched to graft material 104A.

As illustrated, a fold 574 of the graft material of pop up branch structure 124A is created as top 134A is stitched to graft material 104A distal to base 132A of pop up branch structure 124A. Of importance, fold 574 is sufficiently small such that collateral opening 128A remains open and not occluded by graft material 104A allowing a guide wire and/or catheter to be passed through collateral opening 128A in a manner similar to that discussed above in reference to FIG. 2.

In one example, tether 570 is a single stitch between pop up branch structure 124A and graft material 104A facilitating easy removal of tether 570.

Similarly, tether 572 extends through the graft material of pop up branch structure 124B, i.e., is stitched to pop up branch structure 126A, e.g., at top 138A, and is also stitched to the inside of graft material 104A.

As illustrated, a fold 576 of the graft material of pop up branch structure 126A is created as top 138A is stitched to graft material 104A distal to base 136A of pop up branch structure 126A. Of importance, fold 576 is sufficiently small such that collateral opening 130A remains open and not occluded by graft material 104A allowing a guide wire and/or catheter to be passed through collateral opening 130A in a manner similar to that discussed above in reference to FIG. 2.

In one example, tethers 570, 572 are each a single stitch between pop up branch structures 124A, 126A and graft material 104A facilitating easy removal of tethers 570, 572. By tethering each pop up branch structures 124A, 126A to graft material 104A independently using tethers 570, 572, independent and sequential release of pop up branch structures 124A, 126A by removal of tethers 570, 572 is facilitated. For example, tether 570 is removed prior to removal of tether 572.

In other examples, tethers 570, 572 are wires, chords, or other structures that hold pop up branch structures 124A, 126A to graft material 104A. Further, tethers 570, 572 can include knots, loops, clasps or other structures that release pop up branch structures 124A, 126A when pulled.

This disclosure provides exemplary embodiments. The scope is not limited by these exemplary embodiments. Numerous variations, whether explicitly provided for by the specification or implied by the specification or not, such as variations in structure, dimension, type of material and manufacturing process may be implemented by one of skill in the art in view of this disclosure.

What is claimed is:

1. A tethered pop up branch structure stent graft comprising:
   a graft material;
   a first pop up branch structure comprising a first collateral opening within said graft material;
   a second pop up branch structure comprising a second collateral opening within said graft material; and
   a tether tethering said first pop up branch structure to said second pop up branch structure.

2. The tethered pop up branch structure stent graft of claim 1 wherein said tether comprises a structure that anchors said first pop up branch structure to said second pop up branch structure.

3. The tethered pop up branch structure stent graft of claim 1 wherein said tether comprises a single continuous suture.

4. The tethered pop up branch structure stent graft of claim 3 wherein said tether extends through graft material of said first pop up branch structure and through graft material of said second pop up branch structure.

5. The tethered pop up branch structure stent graft of claim 3 wherein said tether comprises:
- a first end; and
- a second end.

6. The tethered pop up branch structure stent graft of claim 1 wherein said tether comprises a single stitch between said first pop up branch structure and said second pop up branch structure.

7. The tethered pop up branch structure stent graft of claim 1 wherein said first pop up branch structure comprises:
- a first top; and
- a first base, wherein said second pop up branch structure comprises:
- a second top; and
- a second base, wherein said tether anchors said first top and said second top inwards of said graft material.

* * * * *